United States Patent [19]

Krstenansky

[11] Patent Number: 4,971,953

[45] Date of Patent: Nov. 20, 1990

[54] ANTICOAGULANT PEPTIDE ALCOHOLS

[75] Inventor: John L. Krstenansky, Cincinnati, Ohio

[73] Assignee: Merrell Dow Pharmaceuticals, Cincinnati, Ohio

[21] Appl. No.: 504,719

[22] Filed: Apr. 3, 1990

Related U.S. Application Data

[63] Continuation of Ser. No. 192,409, May 10, 1988, abandoned.

[51] Int. Cl.$^5$ .................... A61K 37/02; C07K 7/06; C07K 7/08

[52] U.S. Cl. ........................ 514/14; 514/12; 514/13; 514/15; 530/324; 530/325; 530/326; 530/327; 530/328

[58] Field of Search .............. 514/12, 13, 14, 15; 530/324–328

[56] References Cited

U.S. PATENT DOCUMENTS 4,254,023 3/1981 Stewart et al. .................. 530/330
4,654,302 3/1987 Fritz et al. ...................... 435/70
4,668,662 5/1987 Tripier ........................... 530/324

OTHER PUBLICATIONS

S. Bajusz, et al., *Peptides 32*, 473 (1984).
Chemical Abstracts 52:2122 abstracting F. Markwardt, *Z. Physiol. Chem.* 308, 147–56 (1957).
J. Dodt, et al., *FEBS Letters* 165(2), 180–84 (1984).
J. Dodt, et al., *Biol. Chem. Hoppe-Seyler* 366 379–385 (1985).
D. Bagdy, et al., *Methods Enzymol.*, 45 (Proteolytic Enzymes, Pt.B), 674–75 (1976).
S. J. T. Mao, et al., *Anal. Biochem.* 161, 514–18 (1987).
Chang, FEBS vol. 164 pp. 307–313 (1983).
Rudinger, Peptide Hormone, Parsons (Edi.). U Park Press, Baltimore pp. 1–7 (1976).
Krstenansky et al., J. Med. Chem. vol. 30, No. 9 pp. 1688–1691.

*Primary Examiner*—Lester L. Lee
*Attorney, Agent, or Firm*—Stephen L. Nesbitt

[57] ABSTRACT

This invention relates to peptide derivatives which are useful anticoagulant agents.

31 Claims, No Drawings

ANTICOAGULANT PEPTIDE ALCOHOLS

CROSS-REFERENCE TO RELATED APPLICATION

This is a continuation of application Ser. No. 192,409, filed May 10, 1988, now abandoned.

FIELD OF INVENTION

This invention relates to novel peptide alcohols which are useful anticoagulant agents.

BACKGROUND OF INVENTION

Anticoagulants are useful therapeutic agents in the pharmacological treatment of, for example, acute deep venous thrombosis, pulmonary embolism, acute arterial embolization of the extremities, myocardial infarction, and disseminated intravascular coagulation. Proplylactic administration of anticoagulants is believed to prevent a recurrence of embolism in patients with rheumatic or arteriosclerotic heart disease and to prevent certain thromboembolic complications of surgery. Administration of anticoagulants has also been indicated in the treatment of coronary artery and cerebrovascular disease. Arterial thrombosis, particularly in arteries supplying the heart muscle and brain, is a leading cause of death.

Hirudin is a 65 residue polypeptide isolated from the salivary glands of leeches. It is an anticoagulant agent, which is a thrombin specific inhibitor. Although quite potent, clinical use of hirudin isolated from leech extracts seems unlikely because of its limited quantity, expense, and allergic reactions which commonly follow administration of any foreign protein of this size.

Applicants have discovered a specific region of hirudin that is responsible, at least in part, for its anticoagulant activity. This region has been chemically synthesized and certain of its analogs appear to bind to the recognition site of thrombin but not the enzymatic cleavage site which is spatially separate. Binding of the synthetic peptides competitively prevents binding of the fibrinogen to the recognition site of thrombin, a prerequisite to fibrin production and clot formation. Applicants have now prepared certain reduced derivatives of this peptide. The carboxylic acid function of these new derivatives has been reduced to the corresponding alcohol functionality. The peptide alcohols of this invention possess significant anticoagulant activity and their unusual ability to bind only to the recognition site without binding to the cleavage site of thrombin may allow for a scientifically interesting and therapeutically significant adjunct to anticoagulant therapy. Moreover, the presence of the alcohol function may provide for enhanced potency and extended duration of action.

SUMMARY OF THE INVENTION

Peptide derivatives of the formula

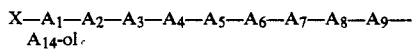

$$X-A_1-A_2-A_3-A_4-A_5-A_6-A_7-A_8-A_9-A_{14}\text{-ol}$$

wherein

X is an amino terminal residue selected from hydrogen, one or two alkyl groups of from 1 to 6 carbon atoms, one or two acyl groups of from 2 to 10 carbon atoms, carbobenzyloxy or t-butyloxy carbonyl;

$A_1$ is a bond or is a peptide containing from 1 to 11 residues of any amino acid;

$A_2$ is Phe, SubPhe, $\beta$-(2- and 3-thienyl)alanine, $\beta$-(2- and 3-furanyl)alanine, $\beta$-(2-, 3-, and 4-pyridyl)alanine, $\beta$-(benzothienyl-2- and 3 -yl)alanine, $\beta$-(1- and 2-naphthyl)alanine, Tyr or Trp;

$A_3$ is Glu or Asp;

$A_4$ is any amino acid;

$A_5$ is Ile, Val, Leu, Nle, or Phe;

$A_6$ is Pro, Hyp, 3,4-dehydroPro, thiazolidine-4-carboxylate, Sar, NMePgl or D-Ala;

$A_7$ is any amino acid;

$A_8$ is any amino acid;

$A_9$ is a lipophilic amino acid selected from Tyr, Met, Trp, Phe, Leu, Nle, Ile, Val, Cha and Pro or is a dipeptide containing at least one of these lipophilic amino acids; and $A_{10}$-ol is a reduced peptide fragment containing from zero to five residues of any amino acid wherein the carbon terminal amino acid is reduced to its alcohol derivative;

are useful anticoagulant agents.

DETAILED DESCRIPTION OF THE INVENTION

The following common abbreviations of the amino acids are used throughout this specification:

Ac—acetyl
Ala (or A)—alanine
DAla (or a)—D-alanine
Arg (or R)—arginine
Asn (or N)—asparagine
Asp (or D)—aspartic acid
pClPhe—para-chloro-phenylalanine
Cha—cyclohexylalanine
Cys (or C)—cysteine
3,4-dehydroPro—3,4-dehydroproline
Gly (or G)—glycine
Glu (or E)—glutamic acid
D-Glu (or e)—D-glutamic acid
Gln (or Q)—glutamine
Glt—glutaryl
His (or H)—histidine
Hyp—hydroxyproline
Ile (or I)—isoleucine
Leu (or L)—leucine
Lys (or K)—lysine
Mal—maleyl
Met (or M)—methionine
NMePgl—N-methyl-phenylglycine
Npa—$\beta$-(naphthyl)alanine
pNO$_2$Phe—para-nitro-phenylalanine
Nle—norleucine
Orn—ornithine
pSubPhe—para substituted phenylalanine
Phe (or F)—phenylalanine
Pgl—phenylglycine
Pro (or P)—proline
Sar—sarcocine (N-methylglycine)
Ser (or S)—serine
SubPhe—ortho, meta, or para, mono- or di- substituted phenylalanine
Suc—succinyl
Thr (or T)—threonine
Trp (or W)—tryptophan
Tyr (or Y)—tyrosine
Val (or V)—valine By the expression "a reduced peptide fragment containing from one to five residues of any amino acid wherein the carbon terminal amino acid is reduced to its alcohol derivative" applicants intend that the carbon atom of the carboxylic acid group of the carbon terminal amino acid is replaced with a hydroxymethyl group, —(CH$_2$)OH. While the A$_{10}$ group of the polypeptides of this invention may contain up to five amino acids, it is intended that only the carbon terminal amino acid be reduced to its corresponding alcohol derivative. Indeed, it is of course not possible that any other but the carbon terminal amino acid be so reduced because peptidic linkage would be impossible. Of course, in those instances wherein A$_{10}$ is a single amino acid, this single acid is the acid reduced to its alcohol derivative. The structural formula for such reduced amino acids can be represented as:

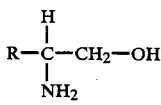

wherein R is the characteristic group of each amino acid. For example, R in the case of glycine is a hydrogen, in the case of alanine is a methyl, in the case of valine is an isopropyl, in the case of phenylalanine is a benzyl, and in the case of cysteine is a mercaptomethyl. The reduced form of proline is an alcohol of the following structural formula.

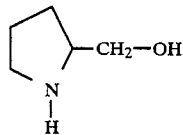

Herein, an amino acid which is reduced to its alcohol derivative will be abbreviated using either the three-letter (or other shortened form) or one-letter code followed by "-ol", for example, "Ala-ol" or "A-ol" means an alanine wherein the carboxylic acid moiety has been reduced to the corresponding alcohol and "Leu-ol" or "L-ol" means a leucine wherein the carboxylic acid moiety has been reduced to the corresponding alcohol.

An alkyl group and the alkyl portion of an alkoxy group is taken to include straight, branched, or cyclic alkyl groups, for example, methyl, ethyl, propyl, isopropyl, butyl, isobutyl, tert-butyl, pentyl, isopentyl, sec-pentyl, cyclopentyl, hexyl, isohexyl, cyclohexyl and cyclopentylmethyl. An acyl group of from 2 to 10 carbon atoms is taken to include straight, branched, cyclic, saturated and unsaturated acyl groups having 1 or 2 carbonyl moieties per group, for example, acetyl, benzoyl succinyl, maleyl, and glutaryl. A halogen group is a fluoro, chloro, bromo or iodo group.

The term "any amino acid" as used herein does not purport to include any carboxylic acid having an amino substitutent, but rather is used as it is commonly used by those skilled in the art of polypeptide derivatives and includes the naturally occurring amino acids as well as other "non-protein" α-amino acids commonly utilized by those in the peptide chemistry arts when preparing synthetic analogs of naturally occurring peptides. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, ornithine, and lysine. Examples of "non-protein" α-amino acids are norleucine, norvaline, alloisoleucine, homoarginine, thiaproline, dehydroproline, hydroxyproline (Hyp), homoserine, cyclohexylglycine (Chg), α-amino-n-butyric acid (Aba), cyclohexylalanine (Cha), aminophenylbutyric acid (Pba), phenylalanines substituted at the ortho, meta, or para-position of the phenyl moiety with one or two of the following, a (C$_1$-C$_4$) alkyl, (C$_1$-C$_4$) alkoxy, halogen, or nitro groups or substituted with a methylenedioxy group, β-2- and 3-thienylal-anine, β-2- and 3-furanylalanine, β-2-, 3-, and 4-pyridylalanine, β-(benzothienyl-2- and 3-yl)alanine, β-(1- and 2-naphthyl)alanine, O-alkylated derivates of serine, threonine, or tyrosine, S-alkylated cysteine, the O-sulfate ester of tyrosine, 3,5-diiodotyrosine and the D-isomers of the naturally occurring amino acids.

The term "lipophilic amino acid" includes Tyr, Phe, Leu, Met, Nle, Ile, Val, His and Pro.

The natural amino acids, with the exception of glycine, contain a chiral carbon atom. Unless otherwise specifically indicated, the optically active amino acids, referred to herein, are of the L-configuration. For example, any of the amino acids of the A$_1$ or A$_{10}$ group can be of the D- or L-configuration. As is customary, the structure of peptides written out herein is such that the amino terminal end is on the left side of the chain and the carboxy terminal end is on the right side of the chain.

The polypeptides of formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and any other suitable amine.

As with any generic group of chemical compounds, certain groups are preferred. Applicants prefer those peptide derivatives of formula 1 wherein X is hydrogen, acetyl, or succinyl. Also preferred are those formula 1 compounds wherein A$_1$ is Thr—Pro—Lys—Pro—Gln—Ser—His—Asn—Asp—Gly—Asp,
—Ser—Thr—Pro—Asn—Pro—
Glu—Ser—His—Asn—Asn—Gly—Asp—,
—His—Asn—Asp—Gly—Asp—,
—Asn—Asp—Gly—Asp—, —Asp—Gly—Asp—,
—Gly—Asp—,
—Asp—, or a bond;

$A_2$ Phe, β-2- or 3-thienylalanine, Tyr, Trp, Npa or pClPhe;

$A_3$, Glu;

$A_4$, Glu, Asp, Pro or Ala;

$A_5$, Ile, Leu;

$A_6$, Pro, Sar, D-Ala, Hyp or NMePgl;

$A_7$, Glu, Gln, Asp or Ala;

$A_8$, Glu, Asp or Ala;

$A_9$, Pro, Ala-Tyr, Ala-Cha, Tyr-Cha, Tyr-Leu, Ala-Phe, Tyr-Tyr;

$A_{10}$-ol, Glu-ol, Asn-ol, Pro-ol, Gln-ol, Ala-ol, D-Lys-ol, Lys-ol, D-Asp-ol, Orn-ol or is Asp-Glu-ol.

Especially preferred are those peptide derivatives of formula 1 wherein either

X is acetyl and $A_1$ is Gly-Asp or Asp or

X is succinyl and $A_1$ is a bond and wherein $A_2$ is Phe; β-(2-thienylalanine) or Tyr;

$A_3$, Glu;

$A_4$, Glu or Pro;

$A_5$, Ile;

$A_6$, Pro;

$A_7$, Glu;

$A_8$, Glu or Asp;

$A_9$, Tyr-Leu, Ala-Tyr, Tyr-Tyr, Ala-Phe, Ala-Cha or Pro; and $A_{10}$-ol, Ala-ol, Gln-ol, Asp-ol, Pro-ol, D-Asp-ol, D-Lys-ol, D-Glu-ol or -Asp-Glu-ol.

The proteins of this invention can be prepared by a variety of procedures readily known to those skilled in the art. Such procedures include the solid phase sequential and block synthesis, gene cloning and combinations of these techniques. The solid phase sequential procedure can be performed using established automated methods such as by use of an automated peptide synthesizer. In this procedure, the peptides were constructed on the resin beginning with the penultimate C-terminal, protected amino acid. The resin support employed can be any suitable resin conventionally employed in the art for the solid phase preparation of polypeptides, preferably polystyrene which has been crosslinked with from 0.5 to about 3 percent divinyl benzene, which has been either chloromethylated or hydroxymethylated to provide sites for ester formation with the initially introduced α-amino protected amino acid. After completion of coupling of the sequence either the Boc protecting group was left in place or it was removed and the N-terminal amino group acylated. Displacement of the protected fragment from the resin was accomplished using the appropriate amino alcohol.

An example of a hydroxymethyl resin is described by Bodanszky et al., Chem. Ind. (London) 38, 1597-98 (1966). A chloromethylated resin is commercially available from Bio Rad Laboratories, Richmond, Calif., and the preparation of such a resin is described by Stewart et al., "Solid Phase Peptide Synthesis" (Freeman & Co., San Francisco 1969), Chapter 1, pp. 1-6. The protected amino acid can be bound to the resin by the procedure of Gisin, Helv. Chem Acta, 56, 1476 (1973). Many resin bound, protected amino acids are commercially available. As an example, to prepare a polypeptide of this invention wherein the carboxy terminal end is a Thr residue, a tert-butyloxycarbonyl (Boc) protected Thr bound to a benzylated, hydroxymethylated phenylacetamidomethyl (PAM) resin can be used and is commercially available.

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and α-chlorobutyryl; (2) aromatic urethan type protecting groups such as benzyloxycarbonyl and substituted benzyloxycarbonyl, such as p-chlorobenzyloxycarbonyl, p-nitrobenzyl- carbonyl, p-bromobenzyloxycarbonyl, p-methoxybenzyloxycarbonyl, 1-(p-biphenylyl)-1-methylethoxycarbonyl, α,α-dimethyl-3,5-dimethoxybenzyloxycarbonyl and benzhydryloxycarbonyl; (3) aliphatic urethan protecting groups such as tert-butyloxycarbonyl (Boc), diisopropylmethoxycarbonyl, isopropyloxycarbonyl, ethoxycarbonyl and allyloxycarbonyl; (4) cycloalkyl urethan type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; and (7) trialkylsilane groups such as trimethylsilane. The preferred α-amino protecting group is tert-butyloxycarbonyl.

The selection of an appropriate coupling reagent is within the skill of the art. A particularly suitable coupling reagent where the amino acid to be added is Gln, Asn or Arg is N,N'-diisopropylcarbodiimide and 1-hydroxybenzotriazole. The use of these reagents prevents nitrile and lactam formation. Other coupling agents are (1) carbodiimides (e.g., N,N'-dicyclohexylcarbodiimide and N-ethyl-N'-(y-dimethylaminopropylcarbodiimide); (2) cyanamides (e.g., N,N-dibenzylcyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-O-Ala-Boc) and (8) nitrogen containing heterocyclic compounds having a hydroxy group on one ring nitrogen (e.g., N-hydroxyphthalimide, N-hydroxysuccinimide and 1-hydroxy-benzotriazole) Other activating reagents and their use in peptide coupling are described by Kapoor, J. Pharm. Sci., 59, pp. 1-27 (1970). Applicants prefer the use of the symmetrical anhydride as a coupling reagent for all amino acids except Arg, Asn and Gln.

Each protected amino acid or amino acid sequence is excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the u-amino protecting group, prior to the coupling of the next amino acid in the solid phase reactor. The success of the coupling reaction at each stage of the synthesis is monitored by the ninhydrin reaction as described by E. Kaiser et al, *Analyt. Biochem.* 34, 595 (1970).

After the desired amino acid sequence has been obtained, the peptide is removed from the resin. This can be done by hydrolysis such as by treatment of the resin bound polypeptide with a the carbon terminal amino alcohol residue, acetic acid, and dichloromethane (DCM).

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed by cleavage during cleavage of the protecting group of the α-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxy-carbonyl, 3,4-dichlorobenzyloxycarbonyl), tosyl, t-amyloxycarbonyl, t-butyloxycarbonyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The preferred protecting group is benzyl.

These groups can be removed by procedures well known in the art. Typically protecting group removal is done after the peptide chain synthesis is complete but the protecting groups can be removed at any other appropriate time. The anticoagulant dose of an alcohol peptide derivative of this invention is from 0.2 mg/kg to 250 mg/kg of patient body weight per day depending on the patient, the severity of the thrombotic condition to be treated and the peptide derivative selected. The suitable dose for a particular patient can be readily determined. Preferably from 1 to 4 daily doses would be administered typically with from 5 mg to 100 mg of active compound per dose. The amount of a peptide alcohol of this invention required to inhibit or prevent blood coagulation in an extracorporeal medium such as stored whole blood can be readily determined by those skilled in the art.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats and mice. Inhibition of blood coagulation is useful not only in anticoagulant therapy of individuals having thrombotic conditions, but is useful whenever inhibition of blood coagulation is desirable, such as to prevent coagulation in stored whole blood and to prevent coagulation in other biological samples for testing or storage.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containing a peptide derivative of this invention in a spray or dry powder form.

For parentral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

EXAMPLES

This invention is illustrated by the following, nonlimiting examples.

EXAMPLE 1

Preparation of Carbon Terminal Peptide Alcohols

The peptides were synthesized using a p-nitrobenzhydrylideneisonitroso resin (oxime resin) prepared by the method of DeGrado and Kaiser (J. Org. Chem. 45, 1295–1300 (1980)). The oxime resin (0.54 g, 0.52 mmol/0.97 mmol/g substitution) was placed in a vessel of an Applied Biosystems Model 430A peptide synthesizer. Boc-protected amino acids were single coupled sequentially as their symmetrical anhydrides in a twofold excess. The side chain protection utilized was as follows: Asp(Chx), Glu(Bzl), Tyr(2-BrZ). The programs of the synthesizer were written to give the following protocol for each cycle:

(1) Add 1 mmol preformed symmetrical anhydride;
(2) Add 5% additional volume of DIEA (?);
(3) Vortex for 1 hour;
(4) Drain;
(5) Wash (5x/1 min.) with DCM;
(6) Wash (1 min.) with 20% TFA in DCM;
(7) Treat with 20% TFA in DCM for 15 minutes;
(8) Wash with DCM (3x/0.5 min.);
(9) Wash (4 min.) with isopropanol

(10) Wash (3x/0.5 min.);
(11) Wash with isopropanol (4 min.);
(12) Wash (3x/0.5 min.) with DCM;
(13) Wash (4 min.) isopropanol;
(14) Wash (3x/0.5 min.).

After completion of the synthesis, the resin was dried in vacuo. The resion was then treated with 2 equivalents (based on the initial resion substitution) of alaninol and 1 equivalent of acetic acid in DCM at room temperature for 20 hours. The resin was filtered. The filtrates were lyophilized. The residue was treated with liquid HF containing 2% anisole at $-5°$ C. for 30 minutes. Upon removal of the HF in vacuo the peptide was extracted with 30% acetonitrile and lyophilized. The residue was purified by preparative HPLC (Dynamax C18 21.4×150 mm column) using an acetonitrile/0.1% TFA system. The peptide obtained by this method gave the desired molecular ion peak by FAB-MS and had an amino acid analysis in accordance with the desired peptide. In this way the following peptides having the stated properties were prepared.

(1) SucFEPIPEEYL-ol
 MW 1092.6 FAB-MS (MH)+1094.0 $t_R$ 17.53
 $E_{280}$ 1573 peptide content 79.8%
 Glx(2) Pro(2) Ile(1) Tyr(1) Phe(1)
 2.08 1.01 0.94 0.99 0.98

(2) SucFEPIPEEYChaA-ol
 MW 1332.7 FAB-MS (MH)+1333.4 $t_R$ 20,2 min.
 $E_{280}$ 1755 peptide content 73%
 Glx(3) Pro(2) Ile(1) Tyr(1) Phe(1) Cha(1)
 3.04 2.03 0.92 1.00 0.97 0.95

(3) SucFEPIPEEYL-ol
 MW 1221.6 FAB-MS (MH)+1222.8 $t_R$ 16.83
 $E_{280}$ 1686 peptide content 72.1%
 Glx(3) Pro(2) Ile(1) Tyr(1) Phe(1)
 3.09 1.98 0.96 0.97 1.00

We claim:

1. An alcohol peptide derivative of the formula

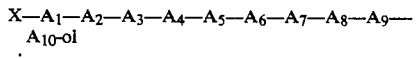

wherein
X is hydrogen, or Suc;
$A_1$ is a bond, Asp, or Gly-Asp;
$A_2$ is Phe or Tyr;
$A_3$ is Glu;
$A_4$ is Glu or Pro;
$A_5$ is Ile;
$A_6$ is Pro;
$A_7$ is Glu;
$A_8$ is Glu, Asp, or Tyr;
$A_9$ is Tyr-Leu, Ala-Tyr, Ala-Phe, Ala-Cha, Tyr-Cha, or Leu;
$A_{10}$ is Gln-ol, Asp-Glu-ol, Pro-ol, D-Lys-ol, Lys-ol, Glu-ol, Asp-ol, or -ol.

2. An alcohol peptide derivative of claim 1 wherein $A_2$ is Phe, or Tyr.

3. An alcohol peptide derivative of claim 1 wherein $A_3$ is Glu.

4. An alcohol peptide derivative of claim 1 wherein $A_4$ is Glu, or Pro.

5. An alcohol peptide derivative of claim 1 wherein $A_5$ is Ile.

6. An alcohol peptide derivative of claim 1 wherein $A_6$ is Pro.

7. An alcohol peptide derivative of claim 1 wherein $A_7$ is Glu.

8. An alcohol peptide derivative of claim 1 wherein $A_8$ is Glu, Asp, or Tyr.

9. An alcohol peptide derivative of claim 1 wherein $A_9$ is Tyr-Leu, Ala-Tyr, Ala-Cha, Ala-Phe, Tyr-Cha, or Leu.

10. An alcohol peptide derivative of claim 1 wherein $A_{10}$-ol is Gln-ol, Asp-ol, Pro-ol, Asp-Glu-ol, Glu-ol, Ala-ol, D-Lys-ol, or Lys-ol.

11. An alcohol peptide derivative of claim 1 wherein X is H, Asp, or succinyl.

12. An alcohol peptide derivative of claim 1 wherein $A_1$ is Gly-Asp or a bond.

13. An alcohol peptide derivative of claim 1 which is H-Gly-Asp-Phe-Glu-Glu-Ile-Pro-Glu-Glu-Tyr-Leu-Gln-ol.

14. An alcohol peptide derivative of claim 1 which is H-Gly-Asp-Phe-Glu-Pro-Ile-Pro-Glu-Asp-Ala-Tyr-Asp-Glu-ol.

15. An alcohol peptide derivative of claim 1 which is Suc-Phe-Glu-Pro-Ile-Pro-Glu-Glu-Tyr-Leu-Pro-ol.

16. An alcohol peptide derivative of claim 1 which is Suc-Phe-Glu-Glu-Ile-Pro-Glu-Glu-Tyr-Leu-Gln-ol.

17. An alcohol peptide derivative of claim 1 which is Suc-Phe-Glu-Pro-Ile-Pro-Glu-Glu-Tyr-Leu-Gln-ol.

18. An alcohol peptide derivative of claim 1 which is Suc-Tyr-Glu-Pro-Ile-Pro-Glu-Glu-Ala-Phe-D-Lys-ol.

19. An alcohol peptide derivative of claim 1 which is Suc-Tyr-Glu-Pro-Ile-Pro-Glu-Glu-Ala-Tyr-Lys-ol.

20. An alcohol peptide derivative of claim 1 which is Suc-Tyr-Glu-Pro-Ile-Pro-Glu-Glu-Ala-Cha-Lys-ol.

21. An alcohol peptide derivative of claim 1 which is Suc-Tyr-Glu-Pro-Ile-Pro-Glu-Glu-Ala-Cha-Lys-ol.

22. An alcohol peptide derivative of claim 1 which is Suc-Tyr-Glu-Pro-Ile-Pro-Glu-Glu-Ala-Phe-Glu-ol.

23. An alcohol peptide derivative of claim 1 which is Suc-Tyr-Glu-Pro-Ile-Pro-Glu-Glu-Ala-Phe-Gln-ol.

24. An alcohol peptide derivative of claim 1 which is Suc-Tyr-Glu-Pro-Ile-Pro-Glu-Glu-Ala-Cha-Asp-ol.

25. A method of reducing blood coagulation in a patient in need thereof which comprises administering an anticoagulant effective amount of an alcohol peptide derivative of one of claims 1–12, 13 or 14–24 and a pharmaceutically acceptable carrier.

26. A method of reducing blood coagulation in a medium which comprises contacting the medium with a blood coagulation, effective amount of an alcohol peptide of one of claims 1–12, 13 or 14–24.

27. An alcohol peptide derivative of claim 1 which is Suc-Phe-Glu-Pro-Ile-Pro-Glu-Tyr-Leu-ol.

28. An alcohol peptide derivative of claim 1 which is Suc-Phe-Glu-Pro-Ile-Pro-Glu-Glu-Tyr-Cha-Ala-ol.

29. An alcohol peptide derivative of claim 1 which is Suc-Phe-Glu-Pro-Ile-Pro-Glu-Glu-Tyr-Leu-ol.

30. An alcohol peptide derivative of claim 1 which is Asp-Phe-Glu-Glu-Ile-Pro-Glu-Glu-Tyr-Leu-Ala-ol.

31. An alcohol peptide derivative of claim 1 which is Asp-Phe-Glu-Glu-Ile-Pro-Glu-Glu-Tyr-Leu-ol.

* * * * *